United States Patent
Grayson

(10) Patent No.: US 7,740,413 B1
(45) Date of Patent: Jun. 22, 2010

(54) DETECTABLE WARNING SYSTEM WITH FIELD THERMOPLASTIC APPLICATION

(76) Inventor: Thomas Grayson, 510 N. Hampton St., Anaheim, CA (US) 92801

( * ) Notice: Subject to any disclaimer, the term of this patent is extended or adjusted under 35 U.S.C. 154(b) by 621 days.

(21) Appl. No.: 11/546,828

(22) Filed: Oct. 12, 2006

Related U.S. Application Data

(63) Continuation-in-part of application No. 10/888,758, filed on Jul. 9, 2004, now Pat. No. 7,142,095, which is a continuation-in-part of application No. 10/716,155, filed on Nov. 18, 2003, now Pat. No. 6,960,989.

(51) Int. Cl.
*E01C 11/24* (2006.01)
*E01C 5/20* (2006.01)

(52) U.S. Cl. .............................. 404/73; 404/12; 404/72; 404/75; 404/94

(58) Field of Classification Search .................. 404/75, 404/19, 15, 79, 12
See application file for complete search history.

(56) References Cited

U.S. PATENT DOCUMENTS

| | | | | |
|---|---|---|---|---|
| 4,715,743 A | * | 12/1987 | Schmanski | 404/9 |
| 5,302,049 A | * | 4/1994 | Schmanski | 404/42 |
| 5,320,780 A | * | 6/1994 | Unruh | 252/500 |
| 5,835,271 A | | 11/1998 | Stump et al. | 359/529 |
| 6,576,074 B1 | * | 6/2003 | Cabrera et al. | 156/71 |
| 6,951,435 B1 | * | 10/2005 | Fennessy, Sr. | 404/75 |
| 6,960,989 B1 | | 11/2005 | Grayson | 340/407.1 |
| 6,971,818 B1 | * | 12/2005 | Schabacker | 404/19 |
| 6,998,010 B2 | * | 2/2006 | Wiley | 156/309.6 |
| 7,142,095 B1 | | 11/2006 | Grayson | 240/407.1 |
| 7,189,025 B1 | * | 3/2007 | Greer et al. | 404/19 |

OTHER PUBLICATIONS

TopMark Brochure, Estimated, Late 2003.
TopMark Material Safety Data Sheet, May 8, 2003.
TopMark Installation Instructions, Jun. 3, 2003.
TopMark Detectable Warning Specification, Jul. 23, 2003.

* cited by examiner

*Primary Examiner*—Raymond W Addie
(74) *Attorney, Agent, or Firm*—Goldstein Law Offices, P.C.

(57) ABSTRACT

A detectable warning system, for tactilely signaling the presence of a terrain transition to a pedestrian, using a plurality of detectable warning domes that are arranged in a grid within a warning dome tiles. The warning dome tiles comprises heat resistant detectable warning domes and connecting surface. A base layer sheet of thermoplastic is applied and adhered to the pavement surface prior to the application of the detectable warning tiles. A top layer of thermoplastic is applied and adhered to, and conformed to the warning domes. The detectable warning domes protrude from the pavement surface in an evenly spaced pattern that is detectable by the pedestrian using a cane or other guidance instrument.

7 Claims, 5 Drawing Sheets

DETECTABLE WARNING SYSTEM WITH FIELD THERMOPLASTIC APPLICATION

CROSS REFERENCES AND RELATED SUBJECT MATTER

This application is a continuation-in-part of patent application Ser. No. 10/888,758, filed in the United States Patent Office on Jul. 9, 2004 now U.S. Pat. No. 7,142,095, which is a continuation-in-part of patent application Ser. No. 10/716,155, now U.S. Pat. No. 6,960,989, filed in the United States Patent Office on Nov. 18, 2003.

BACKGROUND OF THE INVENTION

The invention relates to a detectable warning system. More particularly, the invention relates to a system for easily and effectively creating a field installation of prefabricated detectable warnings to pavement using thermoplastic to provide a tactile warning to pedestrians regarding a hazardous transition.

It is well known that persons with little or no usable vision depend upon environmental cues—ambient sounds, edges and other physical elements that can be sensed by a cane, and texture changes underfoot—for safe and independent travel. People with low vision can also use color contrast as a navigation aid. When raised curbs do not mark and separate the pedestrian route on a sidewalk from the vehicular way, as at curb ramps, vehicle drop-offs, or depressed corners at intersections, it is difficult for some pedestrians to discern the boundary between pedestrian safety and hazard.

Because of the inherent danger caused by transitions without textural changes, the Americans with Disabilities Act Accessibility Guidelines (ADAAG) requires that detectable warnings be installed onto pavement or ground surfaces at certain hazardous junctures. The detectable warnings provide a contrasting texture that signals a hazardous condition to the pedestrian, and thereby informs the pedestrian to exercise care. In particular, the current regulation requires that the detectable warning consist of truncated domes having a nominal diameter of 0.9 inches, protruding from the ground surface to a height of 0.2 inches, and having a center-to-center spacing of 2.35 inches. In addition, the warning should be of contrasting color to effectively warn those who have greatly reduced vision.

In many cases, the warnings must be retrofitted onto existing ground surfaces. Further, the installation of such warnings is not readily compatible with standard paving techniques. Accordingly, the detectable warnings are most typically installed onto already existing pavement surfaces.

Some have proposed systems for the creation and installation of the domes. Generally these systems involve the use of templates to create the dome "in place". Others have proposed systems of prefabricated warning domes. For example, TOP-MARK proposes a system of preformed thermoplastic detectable warnings that is installed in sheets that have a plurality of thermoplastic domes. Unfortunately, the use of thermoplastic warning domes makes the system extremely difficult to install, since heat must be used to install the sheets, but heat will deform or destroy the thermoplastic domes.

My previous U.S. Pat. No. 6,960,989, and the patent that will be issued upon application Ser. No. 10/888,758 describe a system wherein warning domes are encapsulated, covered, or based within thermoplastic prior to field installation. These patents provide a useful reference point for the present invention, and thus are incorporated herein by reference. They do not, however, provide an installation suitable for the most heavy duty use, since the best bonding with the thermoplastic occurs when all surfaces are heated. In addition, thermoplastic looses its dynamic adhesion properties if heated more than once outside of the manufacturing process.

Accordingly, the present invention contemplates application of thermoplastic to the pavement and onto the warning domes at the time of installation onto the recipient pavement surface, which allows heating of all relevant surfaces to create the most effective bond between thermoplastic and other surfaces.

While these units may be suitable for the particular purpose employed, or for general use, they would not be as suitable for the purposes of the present invention as disclosed hereafter.

SUMMARY OF THE INVENTION

It is an object of the invention to provide a system for allowing the effective installation of detectable warnings upon a pavement surface using heat, wherein the warning domes are not harmed during application to said pavement surface. Accordingly, the detectable warnings are made of a heat resistant casting material that is joined to a layer of thermoplastic. The thermoplastic allows the warnings to be effectively mounted and evenly distributed on the pavement surface.

It is another object of the invention to provide a system for allowing the easy fabrication of detectable warning domes carriers for quick and easy subsequent installation of a plurality of domes simultaneously, wherein an installation suitable for heavy duty use an longevity is created. Accordingly, at the installation location, once the pavement is heated, a sheet of opaque thermoplastic is applied to cover the entire installation area and create a base layer. Once the thermoplastic has been heated sufficiently to bond to the pavement, a series of tiles containing a grid of warning domes is laid onto the thermoplastic base layer. Once the tiles have been heated, an additional sheet of thermoplastic is laid upon the tiles to create a top layer. The top layer is itself heated until it closely conforms to the shape of the warning domes therebeneath.

The invention is a detectable warning system, for tactilely signaling the presence of a terrain transition to a pedestrian, using a plurality of detectable warning domes that are arranged in a grid within a warning dome tiles. The warning dome tiles comprises heat resistant detectable warning domes and connecting surface. A base layer sheet of thermoplastic is applied and adhered to the pavement surface prior to the application of the detectable warning tiles. A top layer of thermoplastic is applied and adhered to, and conformed to the warning domes. The detectable warning domes protrude from the pavement surface in an evenly spaced pattern that is detectable by the pedestrian using a cane or other guidance instrument.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
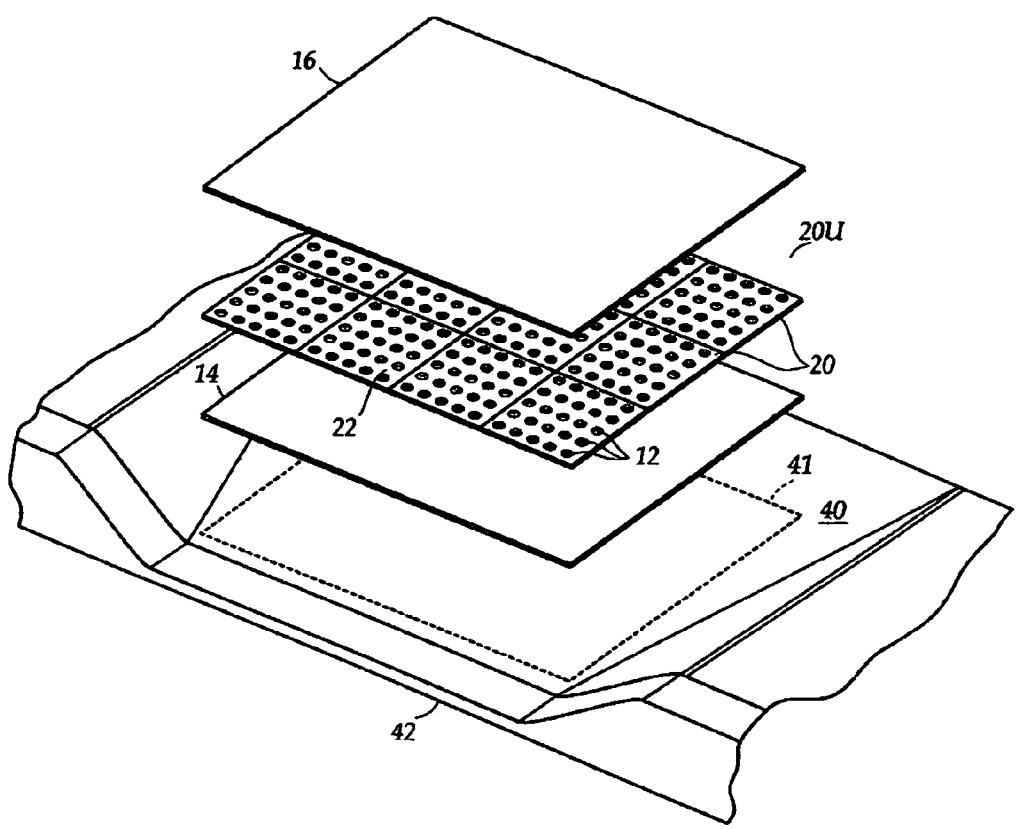
FIG. 1 is a diagrammatic perspective view the various layers of the detectable warning system being installed onto a pavement surface, each layer installed in a separate step according to the present invention.

FIG. 1 illustrates a detectable warning system, for creating an ADAAG compliant warning dome installation on a pavement surface 40 near a hazardous transition point 42. The system includes installation of warning dome tiles 20, a top layer 16, and a base layer 14.

Figure 2:
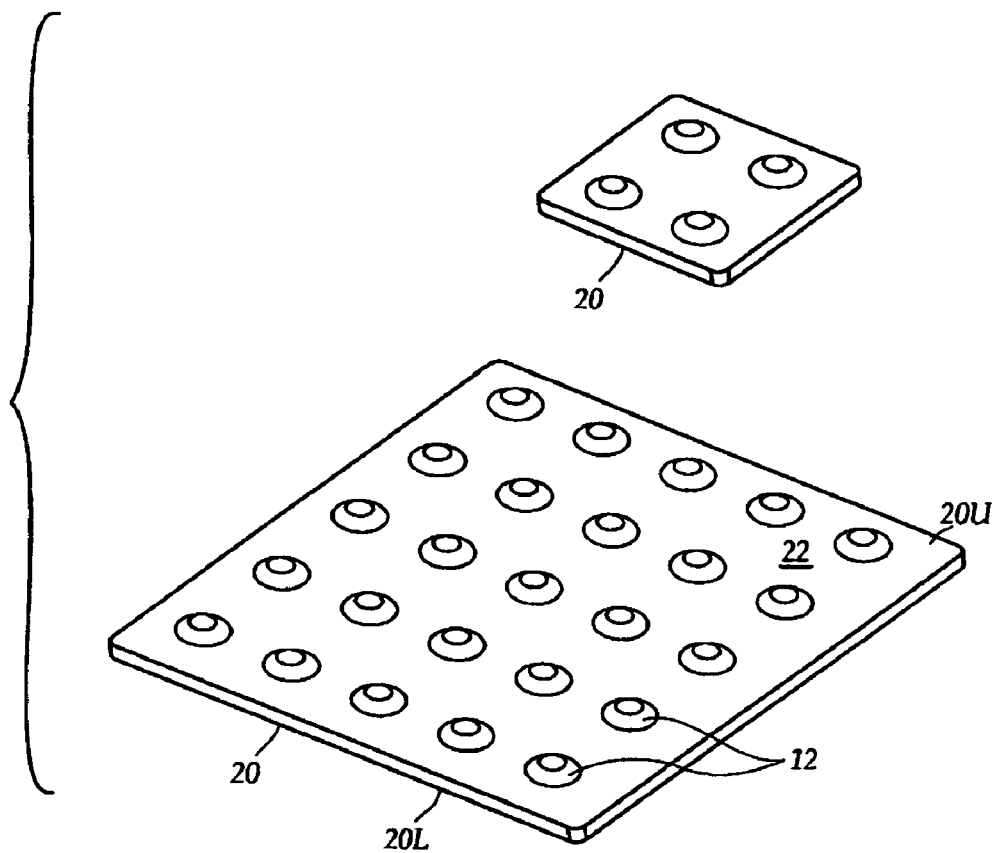
FIG. 2 is a diagrammatic perspective view illustrating different embodiments of the warning dome tiles according to the present invention.

Referring to FIG. 2, two embodiments of the warning dome tiles 20 are illustrated. In particular, the warning dome tiles 20 may comprise a plurality of domes 12 joined and mounted upon a veneer 22 of brick or other earthen material. In particular, the tiles 20 have a lower surface 20L, and an upper surface 20U upon which the domes 12 are mounted. The domes 12 have a truncated shape and are spaced apart as required by regulations such as ADAAG 4.29.2, and to otherwise function as an effective detectable warning. It should be noted that the tiles 20 may be constructed in a variety of ways, including casting the entire tile, including the domes 12 and veneer 22 portions from a heat resistant masonry material. In general, a variety of heat resistant materials can be used for the domes 12, including chemical compounds, mixtures, resins, polymers, organic or inorganic substances, metals or other materials that have heat resistant properties. An important parameter of the heat resistant casting material is that it can resist temperatures of approximately 300-500 degrees Fahrenheit, so as to endure the thermoplastic bonding process during installation.

The use of tiles 20 formed or assembled into a single piece make the detectable warning dome installation thus created durable, and suitable for heavy duty use such as where vehicles or heavy duty equipment may be used. In particular, the veneer 22 helps to spread load and impact forces incident on the individual domes 12. Another advantage of the tiles 20 is that they can be fired in a kiln to remove any moisture that would otherwise deteriorate the longevity of the detectable warning dome installation.

To facilitate proper application of the detectable warning dome tiles 20 onto the pavement surface 40, a base layer 14 and top layer 16 that are sheets of opaque thermoplastic is employed. The use of thermoplastic allows the base layer 14 to melt so as to conform to the contours of the recipient surface, effectively bonding with said recipient surface by flowing into cracks and pores present thereon, and allows the top layer 16 to cover the domes 12 to create a durable and long lasting installation.

Referring again to FIG. 1, as a first step creating the detectable warning dome installation, the pavement surface 40 is heated with a torch to substantially 350 to 450 degrees Fahrenheit. In particular the pavement surface 40 has an installation area 41 which will ultimately be covered by the detectable warning dome installation. It is important to fully heat the installation area 41 to both evaporate moisture from the pavement surface 40 and to ready the same to bond with the thermoplastic.

Once the installation area 41 is hot and moisture has been satisfactorily removed therefrom, the base layer 14 is laid upon the pavement surface to fully overlay the installation area 41. The base layer 14 is heated with a torch or other heating device into a melted or plastic state until the thermoplastic thereof flows into the cracks and pores of the pavement surface 40 and creates an effective bond therewith.

Next, a tile layer is created when the lower surface 20L of the warning dome tiles 20 are laid onto the base layer 14 to substantially cover the installation area 41. As previously noted, the tiles 20 themselves can be different sizes and shapes, containing differing numbers of domes 12. What is important is that they closely abut each other to provide substantially full coverage of the installation area with an essentially continuous surface of warning dome tile 20.

The upper surface 20U of the warning domes tiles 20 are then heated with a torch to substantially 300 to 450 degrees Fahrenheit, to both remove any moisture that might be present and to ready the tiles 20 for the overlay of thermoplastic in the next step. The thermoplastic chosen for the top layer 16 has sufficient thickness to effectively seal the domes 12 and veneer 22 beneath a protective layer of thermoplastic. The top layer 16, however, is substantially thin, such that it does not obscure the contrasting topography of the domes 12 and veneer 22.

When the thermoplastic sheet representing the top layer 16 is laid upon the tiles 20, it substantially covers the tiles 20 and therefore the installation area 41. Then, as a final step in installation, heat is applied to the top layer 16 to between 300 and 450 degrees Fahrenheit. The heat causes the top layer 16 to melt and conform to the topography of the domes 12 and veneer 22, and to create a permanent bond with the tiles 20. The thermoplastic is then left to cool and harden to complete the installation.

Figure 3:
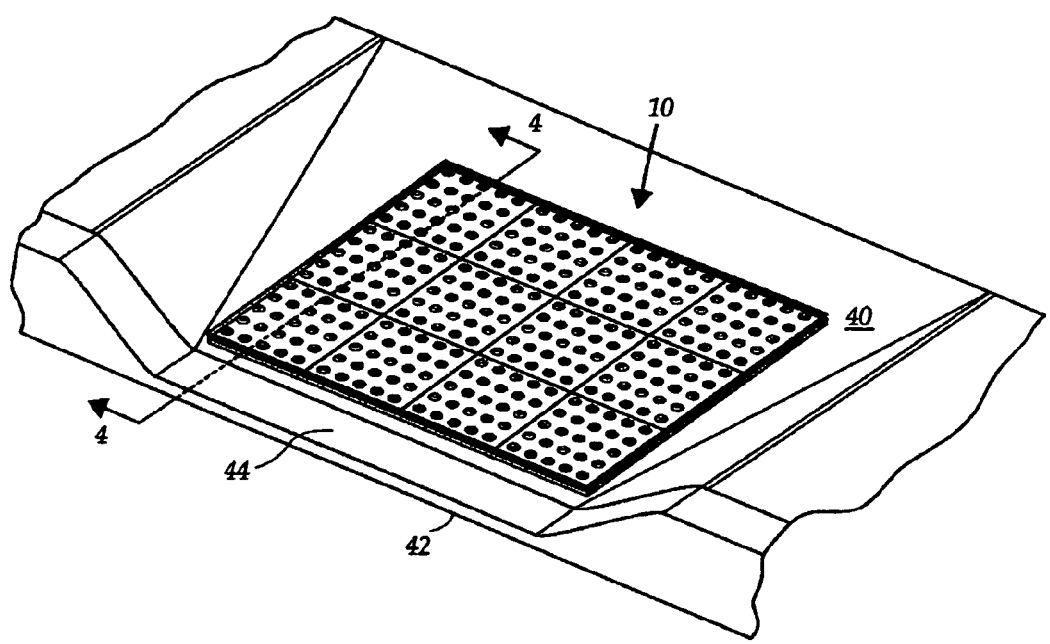
FIG. 3 is a diagrammatic perspective view illustrating the first embodiment of the invention installed onto a pavement surface.
Figure 4:
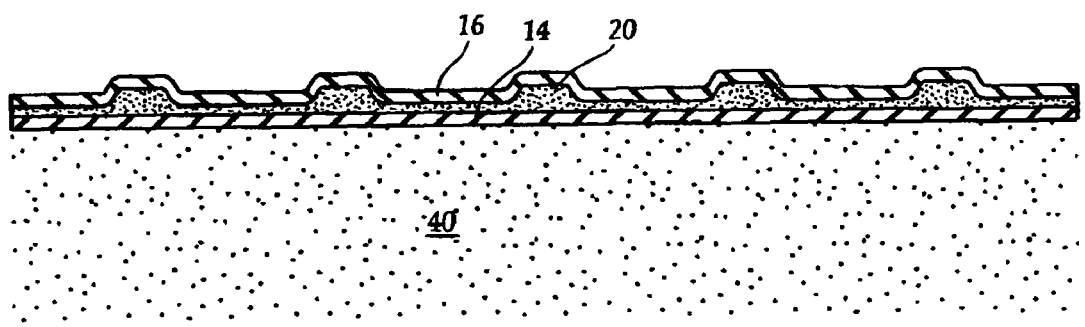
FIG. 4 is a cross sectional view of the detectable warning carrier assembly installed on the pavement surface, as indicated by line 4-4 in FIG. 3, showing the domes sandwiched to the layer of thermoplastic applied during the field installation process of the present invention.

Referring now to FIG. 3, a completed installation of the detectable warning dome system 10 is illustrated. In the environmental context provided within FIG. 3, a curb cut 44 creates the transition point 42 at which it is necessary to provide a textured, tactile warning. In particular, the domes provide tactile feedback to any pedestrian approaching the transition point 42. FIG. 4 is a cross sectional view that illustrates the completed detectable warning dome installation. In particular, the warning dome tiles 20 are bonded to the pavement surface 40 with the base layer 14 and are overlaid with a protective top layer 16 that creates a durable installation suitable for heavy duty use.

Figure 5:
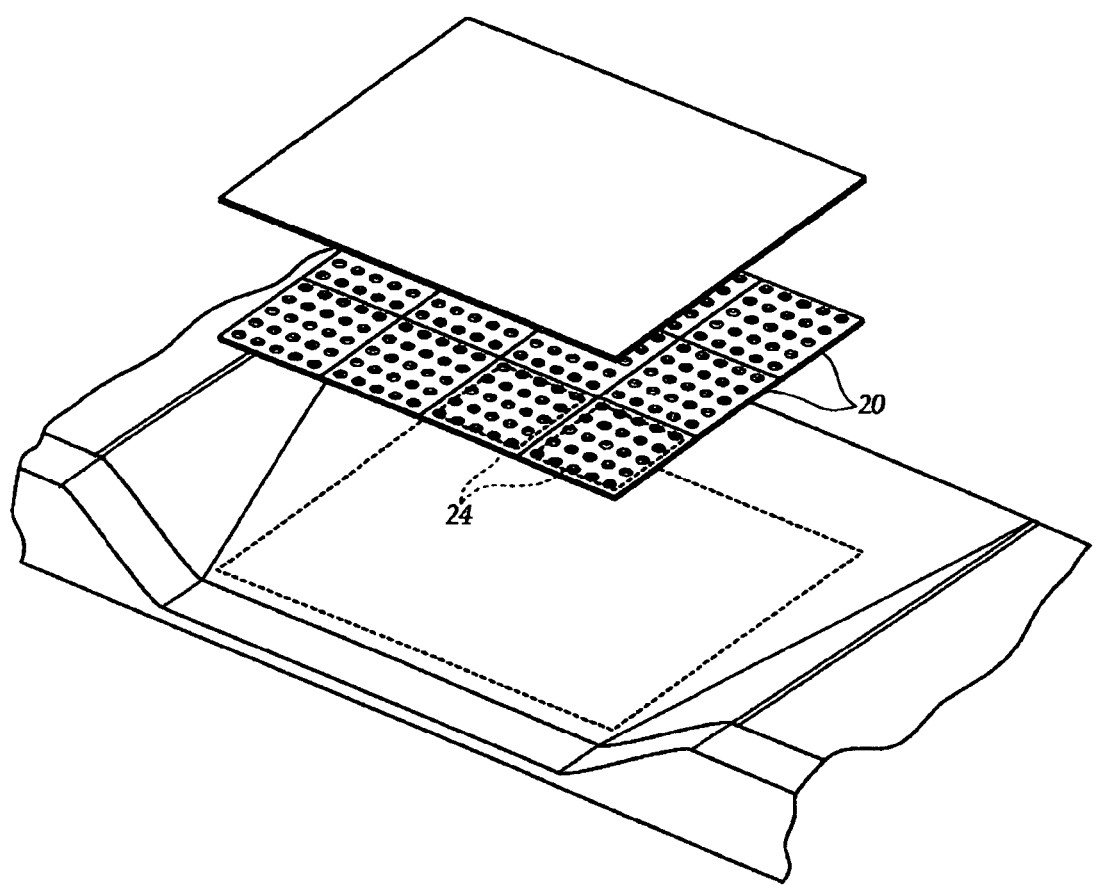
FIG. 5 is a diagrammatic perspective view, illustrating a further embodiment of the invention, wherein the tiles have an adhesive coating on their lower surface, and a base layer of thermoplastic is not used.

By a further embodiment illustrated in FIG. 5, the lower surface 20L of the warning dome is coated with an adhesive material 24. Note that the adhesive used must be sufficient to withstand the heating of the tile during subsequent steps to approximately 450 degrees Fahrenheit. Accordingly, initially the tile layer is created within the installation area by laying the warning dome tiles 20 therein and substantially covering the installation area 41, and bonding the tiles 20 to the pavement surface 40 using the adhesive 24.

Next, as in the previous embodiment, the tiles 20 are heated to retain temperatures between 300 and 450 degrees Fahrenheit. As before, the top layer of thermoplastic 16 is applied to the upper surface 20U of the tiles 20 and is heated to bond thereto.

In conclusion, herein is presented a detectable warning system that is created on a pavement surface using detectable warning dome tiles and sheets of thermoplastic. The invention is illustrated by example in the drawing figures, and throughout the written description. It should be understood that numerous variations are possible, while adhering to the inventive concept. Such variations are contemplated as being a part of the present invention.

What is claimed is:

1. A detectable warning method, for installation onto a pavement surface in an installation area adjacent to a hazardous transition, using a plurality of monolithic warning dome tiles made of heat resistant material and including a veneer having a top surface, lower surface, and a plurality of warning domes arranged in a grid on the top surface of each the plurality of monolithic warning dome tiles, and further using a continuous uninterrupted top layer and a base layer that are sheets of thermoplastic, comprising the steps of:

bonding a base layer of thermoplastic to the pavement surface within the installation area by laying the base layer upon the pavement surface and applying heat directly to the base layer, the base layer being configured to provide leveling and bonding of each the plurality of monolithic warning dome tiles within the installation area;

creating a tile layer within the installation area by laying the lower surface of the plurality of monolithic warning dome tiles upon the base layer to substantially fill the installation area; and bonding a top layer of continuous uninterrupted thermoplastic to the tile layer, within the installation area, by laying the top layer onto the upper surface of each plurality of monolithic warning dome tiles within the installation area to substantially cover the tile layer and applying heat to the top layer.

2. The detectable warning method as recited in claim 1, wherein the step of bonding the base layer is preceded by the step of heating the pavement surface within the installation area remove moisture in the pavement surface and ready the pavement surface for bonding with the base layer.

3. The detectable warning method as recited in claim 2, wherein the step of bonding a top layer of thermoplastic to the tile layer is preceded by the step of heating the upper surface of the tiles to ready the tiles for bonding with the top layer.

4. The detectable warning method as recited in claim 3, wherein the warning dome tiles are made of earthen materials, and wherein the steps as recited are preceded by the step of kiln firing the warning dome tiles to remove moisture therefrom.

5. A detectable warning method, for installation onto a pavement surface in an installation area adjacent to a hazardous transition, using warning dome tiles made of heat resistant material and including a veneer having a top surface, a lower surface having adhesive, and a plurality of warning domes arranged in a grid on the top surface, and further using a top layer is a continuous uninterrupted sheet of thermoplastic, comprising the steps of:

creating a tile layer upon the installation area by laying the lower surface of the warning dome tiles upon the base layer to substantially fill the installation area and bonding the tile layer to the pavement surface with the adhesive; and bonding a top layer of continuous uninterrupted thermoplastic to the tile layer by laying the top layer onto the upper surface to substantially cover the tile layer and applying heat to the top layer.

6. The detectable warning method as recited in claim 5, wherein the step of bond a top layer of thermoplastic to the tile layer is preceded by the step of heating the upper surface of the tiles to ready the tiles for bonding with the top layer.

7. The detectable warning method as recited in claim 6, wherein the warning dome tiles are made of earthen materials.

* * * * *